US008003738B2

(12) United States Patent
Bouillo et al.

(10) Patent No.: US 8,003,738 B2
(45) Date of Patent: Aug. 23, 2011

(54) METHOD OF PRODUCING AQUEOUS SECONDARY DISPERSIONS OF WATER-INSOLUBLE POLYMERS

(75) Inventors: Nathalie Bouillo, Baden-Baden (DE); Gerhard Rößler, Neuhofen (DE)

(73) Assignee: BASF SE, Ludwigshafen (DE)

( * ) Notice: Subject to any disclaimer, the term of this patent is extended or adjusted under 35 U.S.C. 154(b) by 820 days.

(21) Appl. No.: 11/293,246

(22) Filed: Dec. 5, 2005

(65) Prior Publication Data

US 2006/0122321 A1    Jun. 8, 2006

(30) Foreign Application Priority Data

Dec. 7, 2004    (DE) .................. 10 2004 058 952

(51) Int. Cl.
*C08F 2/06*    (2006.01)
*C08F 6/10*    (2006.01)
*C08F 26/10*    (2006.01)
*C08F 26/06*    (2006.01)

(52) U.S. Cl. ........... 526/80; 526/263; 526/264; 524/700

(58) Field of Classification Search ................ 524/700; 526/264, 80

See application file for complete search history.

(56) References Cited

U.S. PATENT DOCUMENTS

| | | | | |
|---|---|---|---|---|
| 4,057,623 A | * | 11/1977 | Hase et al. | 514/772.5 |
| 5,015,708 A | * | 5/1991 | Shih et al. | 526/264 |
| 5,122,582 A | * | 6/1992 | Potthoff-Karl et al. | 526/81 |
| 5,395,904 A | * | 3/1995 | Zhong et al. | 526/264 |
| 5,426,163 A | | 6/1995 | Buehler et al. | |
| 5,506,315 A | * | 4/1996 | Meyer et al. | 526/89 |
| 6,075,107 A | * | 6/2000 | Kothrade et al. | 526/264 |
| 6,107,397 A | * | 8/2000 | Blankenburg et al. | 524/813 |
| 6,436,440 B1 | * | 8/2002 | Meffert et al. | 424/486 |
| 6,727,318 B1 | * | 4/2004 | Mathauer et al. | 524/801 |
| 7,347,938 B2 | * | 3/2008 | Schneider et al. | 210/500.27 |
| 2005/0075453 A1 | * | 4/2005 | Mathauer et al. | 524/801 |

FOREIGN PATENT DOCUMENTS

| | | |
|---|---|---|
| DE | 41 39 963 A1 | 6/1993 |
| WO | WO 00/30595 * | 6/2000 |

OTHER PUBLICATIONS

Lange's Handbook of Chemistry, 15$^{th}$ Edition. McGraw-Hill, 1999.*
ARKEMA 2-Ethylhexyl acrylate MSDS. Available from www.arkema.com. No author. No Date.*
Ki-Chang Lee et al., "Dispersion Polymerization of Styrene and Butyl Acrylate in Isopropanol/Water Media", Korea Polymer Journal, vol. 6, No. 5, (1998), pp. 405-413.
Hanna Bamnolker et al., "Dispersion Polymerization of Styrene in Polar Solvents: Effect of Reaction Parameters on Microsphere Surface Composition and Surface Properties, Size and Size Distribution, and Molecular Weight", Journal of Polymer Science: Part A: Polymer Chemistry, vol. 34, (1996), pp. 1857-1871.
S. Shen et al., "Dispersion Polymerization of Methyl Methacrylate: Mechanism of Particle Formation", Journal of Polymer Science: Part A: Polymer Chemistry, vol. 32, (1994), pp. 1087-1100.

* cited by examiner

*Primary Examiner* — Mark Eashoo
*Assistant Examiner* — Michael A Salvitti
(74) *Attorney, Agent, or Firm* — Connolly Bove Lodge & Hutz LLP

(57) ABSTRACT

The present invention relates to a method of producing aqueous secondary dispersions of water-insoluble copolymers by free-radical solution polymerization of ethylenically unsaturated monomers M comprising:

i) at least one hydrophobic, monoethylenically unsaturated monomer M1 with a solubility in water of not more than 30 g/l at 25° C. and 1 bar and
ii) at least one hydrophilic, monoethylenically unsaturated, nonionic comonomer M2 with a solubility in water of at least 80 g/l at 25° C. and 1 bar, in an organic, water-miscible solvent or a mixture of water with an organic, water-miscible solvent as polymerization medium and subsequent replacement of the organic solvent by water in which, toward the end of the polymerization, some of the monomers M are added in the form of a monomer composition M' which comprises essentially only monomers M2 as monomers. The present invention also relates to the aqueous polymer dispersions obtainable by the method according to the invention and to their use, particularly in pharmacy and cosmetics.

19 Claims, No Drawings

METHOD OF PRODUCING AQUEOUS SECONDARY DISPERSIONS OF WATER-INSOLUBLE POLYMERS

This application claims priority from German Application DE 102004058952.6 filed Dec. 7, 2003, the disclosure of which is incorporated herein by reference.

The present invention relates to a method of producing aqueous secondary dispersions of water-insoluble copolymers by free-radical solution polymerization of ethylenically unsaturated monomers M, comprising:
i) at least one hydrophobic, monoethylenically unsaturated monomer M1 with a solubility in water of not more than 30 g/l at 25° C. and 1 bar and
ii) at least one hydrophilic, monoethylenically unsaturated, nonionic comonomer M2 with a solubility in water of at least 80 g/l at 25° C. and 1 bar,
in an organic, water-miscible solvent or a mixture of water with an organic, water-miscible solvent as polymerization medium and subsequent replacement of the organic solvent by water. The present invention also relates to the aqueous polymer dispersions obtainable by the method according to the invention and to their use, particularly in pharmacy and cosmetics.

Aqueous dispersions of water-insoluble polymers are often produced by free-radical aqueous emulsion polymerization of ethylenically unsaturated monomers in the presence of surface-active substances such as protective colloids and emulsifiers. Free-radical aqueous emulsion polymerization is limited if the monomers to be polymerized comprise relatively large amounts of hydrophilic monomers with good solubility in water, e.g. at least 80 g/l at 25° C. and 1 bar, besides the customarily used monomers with limited solubility in water. The homopolymerization of the monomers with high solubility in water takes place here as a concurrent reaction.

Possible alternatives are the polymerization of such monomers or monomer mixtures in an organic solvent which is able to completely dissolve the monomers to be polymerized. Replacement of the organic solvent by water gives an aqueous dispersion of these polymers. In contrast to the primary dispersions produced by emulsion or suspension polymerization, the aqueous dispersions produced in this way are also referred to as secondary dispersions. To stabilize aqueous secondary dispersions, i.e. to stabilize the polymer particles in the secondary dispersion, it is, however, necessary, before or during replacement of the organic solvent by water, to add surface-active substances, in particular emulsifiers. However, the use of such surface-active substances is not desired in many areas of application, for example in cosmetics and in pharmacy.

On occasion, polyvinylpyrrolidone has been proposed for stabilizing the polymer particles during an emulsion or suspension polymerization of hydrophobic monomers in a polar medium, for example in water or water/$C_1$-$C_4$-alkanol mixtures (see e.g. Korea Polymer Journal 6 (1998), pp. 405-413, J. Polymer Sci., Part A: Polymer Chemistry 34 (1996), pp. 1857-1871 and J. Polymer Sci., Part A: Polymer Chemistry 32 (1994), pp. 1087-1100).

The inventor's own investigations have, however, shown that stable aqueous secondary dispersions cannot be obtained by adding polyvinylpyrrolidone during or after the polymerization of hydrophobic monomers.

The object of the present invention is therefore to provide a method of producing aqueous secondary dispersions of water-insoluble polymers which have been produced by free-radical polymerization of ethylenically unsaturated monomers M according to the method defined at the start.

Surprisingly, it has been found that this object can be achieved by, toward the end of the polymerization, adding some of the monomers M in the form of a monomer composition M' which comprises essentially only monomers M2 as monomers.

The present invention therefore provides a method of producing aqueous secondary dispersions of water-insoluble copolymers comprising
a) free-radical solution polymerization of ethylenically unsaturated monomers M, which comprise
i) at least one hydrophobic, monoethylenically unsaturated monomer M1 with a solubility in water of not more than 30 g/l at 25° C. and 1 bar and
ii) at least one hydrophilic, monoethylenically unsaturated, nonionic comonomer M2 with a solubility in water of at least 80 g/l at 25° C. and 1 bar, in an organic, water-miscible solvent or a mixture of water with an organic, water-miscible solvent as polymerization medium and
b) subsequent replacement of the organic solvent by water, wherein, toward the end of the polymerization, some of the monomers M are added in the form of a monomer composition M' which comprises essentially only monomers M2 as monomers.

The invention is associated with a number of advantages. Firstly, the aqueous secondary dispersions obtainable according to the invention are stable even upon prolonged storage, i.e. they exhibit no or only very slight propensity for coagulation and/or sedimentation. Furthermore, the use of surface-active substances, in particular emulsifiers, is not required for producing the aqueous secondary dispersions according to the invention. The aqueous polymer dispersions obtainable according to the invention are therefore suitable to a particular degree for those applications in which the interface-active substances customarily used in a normal aqueous emulsion polymerization are troublesome or are undesired for other reasons, such as, for example, in cosmetic or pharmaceutical preparations.

The present invention thus further provides the aqueous secondary dispersions obtainable by the method according to the invention and the polymers obtained therefrom by drying. The invention also relates to the use of the thus obtainable secondary dispersions and polymers for producing cosmetic or pharmaceutical preparations. The invention also relates to the use of the polymer powders obtainable from the secondary dispersions for producing cosmetic or pharmaceutical preparations.

According to the invention, the monomers M to be polymerized comprise at least one monoethylenically unsaturated, hydrophobic monomer M1. This is understood as meaning a monomer with a solubility in water of not more than 30 g/l, in particular not more than 10 g/l and specifically not more than 1 g/l at 25° C. and 1 bar.

The monomers M1 usually constitute at least 10% by weight, often at least 15% by weight and in particular at least 20% by weight, of the monomers M in order to ensure adequate insolubility in water of the resulting polymer. Usually, its fraction of the total amount of monomers M will not exceed 90% by weight, often 80% by weight and in particular 70% by weight. Accordingly, the fraction of the monomers M2 of the total amount of the monomers M is usually at least 10% by weight, often at least 20% by weight and in particular at least 30% by weight and will usually not exceed 90% by weight, often 85% by weight and specifically 80% by weight. In a preferred embodiment of the invention, the fraction of the monomers M1 is 10 to 60% by weight, in particular 15 to 50% by weight and specifically 20 to 40% by weight, based on the total amount of the monomers M. Accordingly, in this embodiment, the fraction of the monomers M2 of the total amount of the monomers M is 40 to 90% by weight, in particular 50 to 85% by weight and specifically 60 to 80% by weight.

The monomers M1 include esters of monoethylenically unsaturated $C_3$-$C_8$-carboxylic acids whose alcohol component is a hydrocarbon radical having, for example, 1 to 30 carbon atoms, with the exception of methyl acrylate, also vinyl esters and allyl esters of aliphatic carboxylic acids having 2 to 30 carbon atoms, olefins having 2 to 20 carbon atoms, vinylaromatics such as styrene and alkyl-substituted styrenes, such as α-methylstyrene and tert-butylstyrene, and also N-substituted amides and N,N-disubstituted amides of monoethylenically unsaturated $C_3$-$C_8$ carboxylic acids, wherein the substituent on the nitrogen has 1 to 30 C atoms.

In particular, the method according to the invention is suitable for polymerizing monomers M in which the monomers M1 comprise at least one monomer M1a which has at least one hydrocarbon radical having 6 to 30 carbon atoms and in particular having 8 to 24 carbon atoms. In a preferred embodiment, the monomers M1a constitute at least 50% by weight of the monomers M1 and in particular at least 80% by weight of the monomers M1. In particular, the monomers M1a are the sole monomer M1.

Hydrocarbon radicals having 6 to 30 and in particular 8 to 24 carbon atoms comprise linear or branched alkyl which can have one or two double bonds, in that which follows also $C_6$-$C_{30}$-alkyl, $C_6$-$C_{30}$-alkenyl, $C_6$-$C_{30}$-alkadienyl or $C_8$-$C_{24}$-alkyl, $C_8$-$C_{24}$-alkenyl or $C_8$-$C_{24}$-alkadienyl, such as n-hexyl, n-octyl, 2-ethylhexyl, n-decyl, 2-propylheptyl, lauryl, myristyl, cetyl, stearyl, oleyl and behenyl, also cycloaliphatic radicals which have, if appropriate, 1, 2, 3 or 4 $C_1$-$C_6$-alkyl groups and which in total have 6 to 30 and in particular 8 to 24 carbon atoms (in that which follows $C_6$-$C_{30}$-cycloalkyl), such as cyclohexyl, cycloheptyl, 4-tert-butyl, norbornyl, adamantyl, tricyclo[3.2.1.0]decyl and 3,3,5,5-tetramethylcyclohexyl, and also linear or branched alkyl which carries one or two cycloalkyl radicals and in total has 6 to 30 and in particular 8 to 24 carbons atoms, for example cyclohexylmethyl, cycloheptylmethyl, 2-cyclohexylethyl, bis(cyclohexyl)methyl, 2,2-bis(cyclohexyl)ethyl and 3,3-bis(cyclohexyl)butyl.

The monomers M1a include esters of monoethylenically unsaturated carboxylic acids, in particular those with 3 to 8 carbon atoms and the amides of those monoethylenically unsaturated carboxylic acids, such as acrylic acid or methacrylic acid, which have at least one of the abovementioned hydrocarbon radicals having 6 to 30 and in particular 8 to 24 carbons.

The monomers M1a also include vinyl esters and allyl esters of aliphatic carboxylic acids having 6 to 31 and in particular having 9 to 25 carbon atoms, for example vinyl hexanoate, vinyl octanoate, vinyl laurate, vinyl myristate, vinyl stearate, vinyl oleate and vinyl behenate.

The monomers M1a also include olefins having at least 6 carbon atoms and alkyl-substituted styrene, e.g. tert-butylstyrene.

Among the monomers M1a, esters of monoethylenically unsaturated carboxylic acids, in particular of monocarboxylic acids having 3 to 8 carbon atoms and the amides of such monoethylenically unsaturated carboxylic acids, in particular of monocarboxylic acids having 3 to 8 carbon atoms, which carry at least one of the abovementioned hydrocarbon radicals having 6 to 30 and in particular 8 to 24 carbon atoms, are preferred. Particular preference is given to the esters of acrylic acid with $C_8$-$C_{24}$-alkanols or $C_8$-$C_{24}$-cycloalkanols, esters of methacrylic acid with $C_8$-$C_{24}$-alkanols or $C_8$-$C_{24}$-cycloalkanols, the N—$C_8$-$C_{24}$-alkylamides and the N—$C_8$-$C_{24}$-cycloalkamides of acrylic acid and of methacrylic acid, and the N,N-bis($C_8$-$C_{24}$-alkyl)amides of acrylic acid and of methacrylic acid. Particular preference is given to the abovementioned esters of acrylic acid and of methacrylic acid with $C_8$-$C_{24}$-alkanols, such as n-octyl acrylate, 2-ethylhexyl acrylate, n-decyl acrylate, 2-propylheptyl acrylate, lauryl acrylate, myristyl acrylate, cetyl acrylate, stearyl acrylate, oleyl acrylate and behenyl acrylate, n-hexyl methacrylate, n-octyl methacrylate, 2-ethylhexyl methacrylate, n-decyl methacrylate, 2-propylheptyl methacrylate, lauryl methacrylate, myristyl methacrylate, cetyl methacrylate, stearyl methacrylate, oleyl methacrylate and behenyl methacrylate. Preference is also given to the N—$C_8$-$C_{24}$-alkylamides of acrylic acid and of methacrylic acid, such as n-octylacrylamide, 2-ethylhexylacrylamide, n-decylacrylamide, 2-propylheptylacrylamide, laurylacrylamide, myristylacrylamide, cetylacrylamide, stearylacrylamide, oleylacrylamide and behenylacrylamide, n-hexylmethacrylamide, n-octylmethacrylamide, 2-ethylhexylmethacrylamide, n-decylmethacrylamide, 2-propylheptylmethacrylamide, laurylmethacrylamide, myristylmethacrylamide, cetylmethacrylamide, stearylmethacrylamide, oleylmethacrylamide and behenylmethacrylamide.

The monomers M1 further include monoethylenically unsaturated monomers M1b with a limited solubility in water in the range from >1 g/l to 30 g/l. These include, for example, the $C_1$-$C_4$-alkyl esters of monoethylenically unsaturated carboxylic acids having 3 to 8 C atoms, in particular the esters of acrylic acid and of methacrylic acid, such as ethyl acrylate, n-propyl acrylate, isopropyl acrylate, n-butyl acrylate and tert-butyl acrylate, also methyl methacrylate, ethyl methacrylate, n-propyl methacrylate, isopropyl methacrylate, n-butyl methacrylate and tert-butyl methacrylate, but also vinyl esters of aliphatic carboxylic acids having 2 to 4 carbon atoms, such as vinyl acetate, vinyl propionate and vinyl butyrate.

In a particularly preferred embodiment of the invention, the monomers M comprise 10 to 60% by weight, in particular 15 to 50% by weight and specifically 20 to 40% by weight, of monomers M1a and 40 to 90% by weight, in particular 50 to 85% by weight and 60 to 80% by weight of monomers M2, in each case based on the total weight of the monomers M to be polymerized. In another likewise preferred embodiment, the monomers M comprise 5 to 50% by weight, in particular 10 to 40% by weight of monomers M1a, 10 to 60% by weight, in particular 10 to 50% by weight of monomers M1b and 20 to 85% by weight, in particular 45 to 80% by weight of monomers M2, in each case based on the total weight of the monomers M to be polymerized.

The monomers M2 fundamentally include all nonionic monoethylenically unsaturated monomers with a solubility in water of at least 80 g/l at 25° C. and 1 bar. These include, for example, hydroxy-$C_2$-$C_4$-alkyl esters of monoethylenically unsaturated mono- and di-$C_3$-$C_8$ carboxylic acids, in particular the hydroxy-$C_2$-$C_4$-alkyl esters of acrylic acid and of methacrylic acid, such as 2-hydroxyethyl acrylate, 3-hydroxypropyl acrylate, 2-hydroxypropyl acrylate, 4-hydroxybutyl acrylate, 2-hydroxyethyl methacrylate, 3-hydroxypropyl methacrylate, 2-hydroxypropyl methacrylate and 4-hydroxybutyl methacrylate;

N-vinyllactams, in particular those with 5 to 8 ring atoms, such as N-vinyl-pyrrolidone, N-vinylpiperidone, N-vinylmorpholinone and N-vinylcaprolactam, N-vinylamides of aliphatic carboxylic acid having 1 to 6 and in particular 1 to 4 carbon atoms, such as N-vinyl-formamide, N-vinylacetamide and N-vinyl-propionamide;

amides, hydroxy-$C_1$-$C_4$-alkylamides and $C_1$-$C_4$-alkyloxy-$C_1$-$C_4$-alkylamides of monoethylenically unsaturated $C_3$-$C_8$-monocarboxylic acids, such as acrylamide; methacrylamide, N-(methoxymethyl)(meth)acrylamide, N-(ethoxymethyl)-(meth)acrylamide, N-(2-methoxyethyl)(meth)acrylamide, N-(2-ethoxyethyl)-(meth)acrylamide and the like;

monoethylenically unsaturated monomers with polyether groups, in particular with poly-$C_2$-$C_4$-alkylene oxide groups, especially with polyethylenoxide groups, where the polyether groups preferably have a molecular weight (number average) in the range from 100 to 5000. These include, in particular, the vinyl and allyl ethers of poly-$C_2$-$C_4$-alkylene glycols, and the monoesters of monoethylenically unsaturated $C_3$-$C_8$-mono- and $C_4$-$C_8$-dicarboxylic acids with poly-$C_2$-$C_4$-alkylene glycols, in particular the acrylic and the methacrylic monoesters of such poly-$C_2$-$C_4$-alkylene glycols vinyl-substituted nitrogen heteroaromatics, such as 2-, 3- and 4-vinylpyridine and N-vinylimidazole;

monoethylenically unsaturated monomers carrying urea groups, such as N-(2-acrylamidoethyl)imidazolin-2-one and N-(2-methacrylamidoethyl)imidazolin-2-one;

esters and amides of the abovementioned monoethylenically unsaturated carboxylic acids having aldehyde or keto groups, such as 3-(acrylamido)-3-methylbutan-2-one (diacetone acrylamide), 3-(methacrylamido)-3-methylbutan-2-one, 2,4-dioxapentyl acrylate and 2,4-dioxapentyl methacrylate; and monoethylenically unsaturated monomers with a primary, secondary or tertiary amino group, in particular monomers of the general formula I

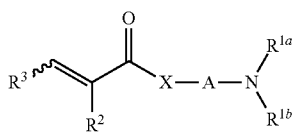

(I)

in which X is oxygen or a group N—$R^4$;

A is $C_2$-$C_8$-alkylene, e.g. 1,2-ethanediyl, 1,2- or 1,3-propanediyl, 1,4-butanediyl or 2-methyl-1,2-propanediyl, which is optionally interrupted by 1, 2 or 3 nonadjacent oxygen atoms, as in 3-oxapentane-1,5-diyl, $R^{1a}$, $R^{1b}$, independently of one another, are hydrogen, $C_1$-$C_{10}$-alkyl, $C_5$-$C_{10}$-cycloalkyl, phenyl or phenyl-$C_1$-$C_4$-alkyl and, in particular, the two together are $C_1$-$C_4$-alkyl;

$R^2$ is hydrogen or $C_1$-$C_4$-alkyl, in particular hydrogen or methyl;

$R^3$ is hydrogen or $C_1$-$C_4$-alkyl, in particular hydrogen; and $R^4$ is hydrogen or $C_1$-$C_4$-alkyl and in particular hydrogen.

Examples of monomers of the formula I are 2-(N,N-dimethylamino)ethyl acrylate, 2-(N,N-dimethylamino)ethyl methacrylate, 2-(N,N-dimethylamino)ethylacrylamide, 3-(N,N-dimethylamino)propylacrylamide, 3-(N,N-dimethylamino)propylmeth-acrylamide and 2-(N,N-dimethylamino)ethylmethacrylamide.

In a preferred embodiment, the monomers M2 are chosen from the abovementioned N-vinyllactams having 5 to 8 ring atoms and the N-vinylamides of aliphatic carboxylic acids having 1 to 6 and in particular 1 to 4 carbon atoms. Particularly preferred monomers M2 are the abovementioned N-vinyllactams and in particular N-vinylpyrrolidone.

If appropriate, the monomers M to be polymerized can also comprise up to 20% by weight and in particular up to 10% by weight, e.g. 0.05 to 10% by weight, of monomers M3, which are different from the monomers M1 and M2. The monomers M3 include monoethylenically unsaturated monomers M3.s, which have at least one acid group or at least one anionic group, in particular monomers which have a sulfonic acid group, a phosphonic acid group or one or two carboxylic acid groups, and the salts of such monomers, in particular the alkali metal salts, e.g. the sodium or potassium salts, and the ammonium salts. These include ethylenically unsaturated sulfonic acids, in particular vinylsulfonic acid, 2-acrylamido-2-methylpropanesulfonic acid, 2-acryloxyethanesulfonic acid and 2-methacryloxyethanesulfonic acid, 3-acryloxy- and 3-methacryloxypropanesulfonic acid, vinylbenzenesulfonic acid and salts thereof, ethylenically unsaturated phosphonic acids, such as vinylphosphonic acid and vinylphosphonic dimethyl ester and salts thereof and α,β-ethylenically unsaturated $C_3$-$C_8$-mono- and $C_4$-$C_8$-dicarboxylic acids, in particular acrylic acid, methacrylic acid, crotonic acid, maleic acid, fumaric acid and itaconic acid. The fraction of the monomers M3.s will often constitute not more than 10% by weight, e.g. 0.05 to 10% by weight and in particular 0.1 to 5% by weight, based on the total amount of the monomers M. In a preferred embodiment, the monomers M comprise no or not more than 0.1% by weight of monomers M3.s.

The monomers M3 further include monoethylenically unsaturated monomers M3.k which have at least one cationic group. The monomers M3.k include, in particular, those which have a quaternary ammonium group or a quaternized imino group.

Examples of monomers with a quaternized imino group are N-alkylvinylpyridinium salts and N-alkyl-N'-vinylimidazolinium salts, such as N-methyl-N'-vinylimidazolinium chloride or metosulfate, and also ω-(tri-$C_1$-$C_4$-alkylammonium)-$C_2$-$C_4$-alkyl acrylates, ω-(tri-$C_1$-$C_4$-alkylammonium)-$C_2$-$C_4$-alkyl methacrylates, ω-(tri-$C_1$-$C_4$-alkylammonium)-$C_2$-$C_4$-alkylacrylamides and ω-(tri-$C_1$-$C_4$-alkylammonium)-$C_2$-$C_4$-alkylmethacrylamides, such as 2-(N,N,N-trimethylammonium)ethyl acrylate chloride, 2-(N,N,N-trimethyl-ammonium)ethyl methacrylate chloride, 2-(N,N,N-trimethylammonium)ethyl-methacrylamide chloride, 3-(N,N,N-trimethylammonium)propylacrylamide chloride, 3-(N,N,N-trimethylammonium)propylmethacrylamide chloride, 2-(N,N,N-trimethyl-ammonium)ethylacrylamide chloride, and the corresponding metosulfates and sulfates.

The fraction of the monomers M3.k of the monomers M is advantageously not more than 20% by weight, e.g. 0.1 to 20% by weight, in particular 0.1 to 15% by weight, and specifically 1 to 10% by weight. In a preferred embodiment, the monomers M can comprise no or not more than 0.1% by weight of monomers M3.k.

According to the invention, the monomers M2 present in the monomer composition M' are essentially the sole monomer constituent of M', i.e. the fraction of monomers M2 is more than 90% by weight and in particular more than 99% by weight of all monomers present in the monomer composition M'. Small amounts of other monomers, however, are not disadvantageous. The monomer composition M' can comprise the monomer constituent in undiluted form or in dissolved or diluted form. Besides water, suitable solvents are the organic solvents used for the polymerization and mixtures thereof with water. Preferably, the monomer concentration in the monomer composition is at least 50% by weight, in particular at least 70% by weight.

According to the invention, the monomers M2 present in the remaining fraction of the monomers M are different from or identical to the monomers M2 present in the monomer composition M'. Often, however, the monomers M2 in the monomer composition M' will be the same type of monomers as in the remaining amount of the monomers M.

For the method according to the invention, it is advantageous if the monomers M2 present in the monomer composition M' are chosen from the abovementioned N-vinyllactams having 5 to 8 ring atoms and the N-vinylamides of aliphatic carboxylic acids having 1 to 6 and in particular 1 to 4 carbon atoms. Particularly preferred monomers M2 are the abovementioned N-vinyllactams and in particular N-vinylpyrrolidone, and mixtures of the abovementioned monomers M2 with N-vinyllactams and specifically with N-vinylpyrrolidone which comprise up to 50% by weight, e.g. 1 to 50% by weight, but in particular not more than 30% by weight and particularly preferably not more than 10% by weight, based on the total amount of monomers M2, of monomers M2 different from N-vinylpyrrolidone. In particular N-vinylpyrrolidone is the sole monomer M'.

The fraction of the monomers M2 added via the monomer composition M' is usually 1 to 50% by weight, in particular 2 to 30% by weight and specifically 5 to 20% by weight of the total amount of the monomers M2 to be polymerized.

The amount of monomers (monomers M') introduced via the monomer composition M' is generally at least 0.5% by weight and will in particular not exceed 25% by weight, based on the total amount of the monomers M to be polymerized. Preferably, it is in the range from 1 to 20% by weight, in particular in the range from 3 to 15% by weight and particularly preferably in the range from 5 to 13% by weight, based on the total amount of the monomers M to be polymerized.

The polymerization of the monomers M takes place under the conditions customary for a free-radical polymerization in an organic solvent, in the presence of compounds which form free radicals, so-called initiators. The initiators are usually used in amounts up to 10% by weight, preferably 0.05 to 15% by weight and in particular 0.2 to 5% by weight, based on the monomers M+M' to be polymerized. For initiators consisting of two or more constituents (initiator systems, e.g. in the case of redox initiator systems), the weights given above refer to the sum of the components.

Suitable initiators are, for example, organic peroxides and hydroperoxides, also peroxodisulfates, percarbonates, peroxide esters, hydrogen peroxide and azo compounds. Examples of initiators are hydrogen peroxide, dicyclohexyl peroxydicarbonate, diacetyl peroxide, di-tert-butyl peroxide, diamyl peroxide, dioctanoyl peroxide, didecanoyl peroxide, dilauroyl peroxide, dibenzoyl peroxide, bis(o-tolyl)peroxide, succinyl peroxide, methyl ethyl ketone peroxide, di-tert-butyl hydroperoxide, acetylacetone peroxide, butyl peracetate, tert-butyl permaleinate, tert-butyl perisobutyrate, tert-butyl perpivalate, tert-butyl peroctoate, tert-butyl perneodecanoate, tert-butyl perbenzoate, tert-butyl hydroperoxide, cumene hydroperoxide, tert-butyl perneodecanoate, tert-amyl perpivalate, tert-butyl perpivalate, tert-butyl perbenzoate, tert-butyl peroxy-2-ethylhexanoate and diisopropyl peroxydicarbamate; also lithium, sodium, potassium and ammonium peroxodisulfate, 2,2'-azobisisobutyronitrile, 2,2'-azobis(2-methylbutyronitrile), 2,2'-azobis[2-methyl-N-(2-hydroxyethyl)]propionamide, 1,1'-azobis(1-cyclohexanecarbonitrile), 2,2'-azobis(2,4-dimethylvaleronitrile), 2,2'-azobis(N, N'-dimethyleneisobutyroamidine)dihydrochloride, and 2,2'-azobis(2-amidinopropane) dihydrochloride, and redox initiator systems explained below.

Redox initiator systems comprise at least one oxidizing, generally a peroxide compound and at least one reducing compound, for example a reducing sulfur compound, such as bisulfites, sulfites, thiosulfates, dithionites, tetrathionates of alkali metals or ammonium salts thereof or an organic reducing agent, such as benzoine, dimethylaniline, ascorbic acid, hydroxymethanesulfinates, and adducts of hydrogensulfite onto ketones, such as, for example, the acetone-bisulfite adduct.

In combination with the initiators or the redox initiator systems it is additionally possible to use transition metal catalysts, e.g. salts of iron, cobalt, nickel, copper, vanadium and manganese. Suitable salts are, for example, iron(II) sulfate, cobalt(II) chloride, nickel(II) sulfate, or copper(I) chloride. Based on the monomers, the reducing transition metal salt is used in a concentration of from 0.1 ppm to 1000 ppm. It is thus possible to use combinations of hydrogen peroxide with iron(II) salts, such as, for example, 0.5 to 30% hydrogen peroxide and 0.1 to 500 ppm of Mohr's salt.

Preferred initiators are organic peroxides and hydroperoxides, and redox initiators which comprise one of the abovementioned organic peroxides or hydroperoxides.

If appropriate, it may be required to control the molecular weight of the polymers to be produced. For this purpose, the polymerization of the monomers M is generally carried out in the presence of regulators. The regulators include, for example, organic compounds containing SH groups, in particular water-soluble compounds containing SH groups, such as 2-mercaptoethanol, 2-mercaptopropanol, 3-mercaptopropionic acid, cysteine and N-acetylcysteine. The polymerization regulators are, if desired, generally used in amounts of from 0.05 to 2% by weight, in particular 0.1 to 1% by weight, based on the monomers M.

According to the invention, the polymerization of the monomers M takes places in an organic solvent which is miscible with water, or in a mixture which comprises at least one water-miscible organic solvent and water. In these mixtures, the fraction of water is preferably not more than 50% by weight, e.g. 1 to 50% by weight, in particular not more than 40% by weight, e.g. 2 to 40% by weight, particularly preferably not more than 30% by weight, e.g. 5 to 30% by weight, based on the total amount of water plus organic solvent.

Here and below, water-miscible solvents are those organic solvents which, at 25° C. and 1 bar, form a homogeneous phase with 50 parts by weight of water, based on 100 parts by weight of organic solvent. These include preferably protic solvents, such as $C_1$-$C_4$-alkanols, e.g. methanol, ethanol, n-propanol, isopropanol, n-butanol, cyclic ethers, such as tetrahydrofuran and dioxane, ketones, such as acetone, methyl ethyl ketone and cyclohexanone, glycols and glycol ethers, such as ethylene glycol, propylene glycol, ethylene glycol monomethyl ether, diethylene glycol, triethylene glycol, diethylene glycol monomethyl ether and triethylene glycol monomethyl ether.

Preferred organic solvents are $C_1$-$C_4$-alkanols. In particular, the method according to the invention is carried out in a $C_1$-$C_4$-alkanol or in a mixture of a $C_1$-$C_4$-alkanol with water in the quantitative ratios given above.

According to the invention, toward the end of the polymerization, the monomer composition M' is added. This means that the addition of the monomer composition M' usually takes place at a time when at least 80%, in particular at least 90% and particularly preferably at least 95%, of that fraction of the monomers M which is different from the monomers M', thus does not belong to the monomer composition M', is already present in the polymerization vessel under polymerization conditions. In the case of a monomer feed method, this is the case when at least 80%, preferably at least 90% and in particular at least 95%, of this monomer fraction has been introduced into the polymerization vessel. In particular, the addition of the monomer composition M' and its polymerization takes place when the total amount of this monomer fraction is already present in the polymerization vessel, in the case of a polymerization by a monomer feed method after addition of this monomer fraction is complete. The addition of the monomer composition M' can take place in one portion, in two or more portions or continuously over an extended period. Preferably, the monomer composition M' is added over a period of from 10 minutes to 1 h.

The polymerization of the monomers present in the monomer composition M' takes place during or after the addition of the monomer composition M'. The polymerization of the monomers M' is triggered like the polymerization of the monomers M by a polymerization initiator. Suitable polymerization initiators for the polymerization of the monomers M' are the initiators specified above and in particular the polymerization initiators specified there as being preferred.

For the polymerization of the fraction of the monomers M different from the monomers M' it has proven useful to work in accordance with a monomer feed method. In this, the majority of the monomers to be polymerized, preferably at least 70% by weight, e.g. 70 to 99% by weight and in particular at least 80% by weight, e.g. 80 to 95% by weight, of the monomers to be polymerized, is introduced as monomer feed to the polymerization reaction as it proceeds. In principle, the monomer feed can comprise the whole amount of the monomers different from the monomers M'. However, preferably about 1 to 30% by weight and in particular 2 to 20% by weight of the monomers M to be polymerized are initially introduced into the reaction vessel. To initiate polymerization, the initial charge is heated to the polymerization temperature and then the addition of the remainder of the monomers and of the remainder of polymerization initiator is started. The addition of the monomers and of the polymerization initiator is generally matched in terms of time to the other and can take place in portions, at intervals or continuously with constant or variable feed rate. The monomers can be added either in the form of the pure monomers or else in a solution of these monomers in the organic solvent or in the mixture of organic solvent and water. The concentration of the monomers in the feed is generally in the range from 10 to 70% by weight and in particular in the range from 30 to 60% by weight, based on the total amount of the monomer feed.

The reaction temperature required for the polymerization of the monomers M is usually in the range from 20 to 150° C. and in particular in the range from 50 to 110° C., depending on the initiator system used in each case. The reaction pressure is of minor importance and it is in the range from 800 mbar to 1.2 bar. As a rule, the reaction is carried out at ambient pressure or under the vapor pressure of the reaction mixture which prevails during the polymerization. The polymerization is preferably carried out in an inert atmosphere, for example under argon or a stream of nitrogen.

The initiator triggering the polymerization can be initially introduced into the polymerization vessel and is preferably added at least partially over the course of the polymerization. The polymerization initiator can be added in portions, at intervals or continuously with constant or variable feed rate. The polymerization initiator is preferably added in the form of a solution in the organic solvent or in a mixture of the organic solvent with water. During the polymerization, solvent or solvent/water is used in an amount to ensure a concentration of monomer or monomer plus polymer in the range from 10 to 70% by weight and in particular 30 to 60% by weight, based on the total amount of polymer, monomer, organic solvent and, if appropriate, water in the polymerization vessel.

In order to ensure polymerization of the monomers M', the polymerization conditions will of course be chosen such that, at the time of adding the monomer composition M', still unused polymerization initiator is present in the polymerization vessel or the required amount of polymerization initiator will be added with the monomers M'. Preference is given to a procedure which involves adding the majority of the polymerization initiator, advantageously at least 80% and in particular at least 90%, to the polymerization vessel over a prolonged period under polymerization conditions. In particular, the addition rate will be chosen such that, at the time of adding the monomers M', 1 to 50%, in particular 2 to 30%, of the total amount of polymerization initiator is still not present in the polymerization vessel. In particular, the procedure will involve the initiator addition not ending before the addition of the monomer composition M' is complete.

If appropriate, the polymerization of the monomers M' can be followed by an after-polymerization, i.e. the polymerization conditions are maintained after the addition of the monomers M' is complete for some time afterwards, e.g. for a period from 10 min to 5 h.

The polymerization method can also be followed by a chemical or physical deodorization. As a rule, however, a deodorization is dispensed with since upon removing the solvent the majority of nonpolymerized monomers and other volatile impurities are likewise removed.

In this way, a solvent-containing polymerization mixture is obtained. According to the invention, the organic solvent is then removed and the solvent is replaced by water. Replacement of the organic solvent by water can be achieved by conventional methods for example by removing the organic solvent by distillative means and successively or continuously replacing it by water. This gives the aqueous secondary dispersions according to the invention of the water-insoluble polymers produced by this method.

The aqueous secondary dispersions obtainable by the method according to the invention are characterized by high stability to sedimentation and coagulation, even after prolonged storage, for example after storage from 4 to 6 weeks or during storage at elevated temperature. They are likewise provided by the present invention.

The aqueous secondary dispersions usually comprise the copolymer obtainable by the method according to the invention in an amount of from 5 to 60% by weight, in particular in an amount of from 10 to 30% by weight.

The K value (in accordance with Fikentscher—Cellulosechemie 1932, Vol. 13, pp. 58-64 and pp. 71-74) of the copolymers obtainable according to the invention is typically in the range from 20 to 100 and in particular in the range from 20 to 80 (determined as a solution in ethanol or isopropanol at 25° C. at a concentration, dependent on the K value, in the range from 0.1 to 5% by weight).

For reasons of improved stability toward sedimentation and coagulation, it is not necessary to add surfactants such as emulsifiers or protective colloids during the production of the aqueous polymer dispersion. Therefore, in a preferred embodiment of the invention, no or less than 0.5% by weight, based on the total weight of the monomers M, of surface-active compounds will be added.

For reasons of improved stability toward sedimentation and coagulation, the aqueous secondary dispersions according to the invention can be easily converted into a powder. The invention therefore also provides polymer powders which are obtainable by drying the aqueous secondary dispersions according to the invention, i.e. by removing the water and other volatile components of the secondary dispersions.

The safety risks and technical problems naturally associated with the drying of solvent-containing polymerization mixtures do not arise during the drying of the aqueous secondary dispersion according to the invention.

The drying of the aqueous secondary dispersions can take place in the usual manner, e.g. by spray-drying, freeze-drying, fluidized-bed drying, drying in an extruder and drum drying. If appropriate, a small amount, e.g. 0.05 to 2% by weight, in particular 0.1 to 1% by weight, based on the polymer to be dried, of spray-drying auxiliaries are added during drying to prevent or reduce clumping of the polymer. Suitable spray-drying auxiliaries are, in particular, silicas, in particular pyrogenic silicas, which are, if appropriate, hydrophobicized.

The secondary dispersions obtainable according to the invention and the polymers present therein are suitable for many application purposes, in particular for producing pharmaceutical or cosmetic preparations. This is true in particular for the copolymers of the monomers M1 with M2, and if appropriate, with M3, which are suitable, for example, for producing cosmetic water-in-oil emulsions as described in DE-A 2514100, as thickeners for hydrophobic liquids as described in DE 10108387, and for producing solid cosmetic and pharmaceutical administration forms as described in EP-A 953358 or WO 99/27916.

The examples below are intended to illustrate the invention without limiting it.

Example 1

Production of an Aqueous Secondary Dispersion by Polymerization of N-vinylpyrrolidone with Stearyl Methacrylate in the Weight Ratio 7:3 in n-propanol 17 g of stearyl methacrylate, 39 g of N-vinylpyrrolidone in 100 g of n-propanol were initially introduced into a polymerization vessel and heated to an internal temperature of 77° C. under a nitrogen atmosphere. Then, with stirring and while retaining the temperature, feed 1 was added over the course of 5.5 h and feed 2 was added over the course of 6.5 h. When feed 1 was complete, the addition of feed 3 was started over the course of 30 minutes. When feed 2 was complete, the temperature was maintained for a further 120 minutes. A mixture of water and n-propanol then started to be distilled off, with the addition of water, until the content of n-propanol in the distillation bottom had dropped to <1% by weight. In this way, an aqueous secondary dispersion with a solids content of 21% by weight was obtained, which showed no signs of sedimentation or coagulation even after storage for four weeks at room temperature. The K value of the polymer (in accordance with Fikentscher see above, measured as 1% strength solution in ethanol at 25° C.) was 45.

Feed 1: 195 g of vinylpyrrolidone, 103 g of stearyl methacrylate, 240 g of n-propanol Feed 2:

2.25 g of tert-butyl peroxopivalate 57 g of n-propanol

Feed 3:

46 g of N-vinylpyrrolidone 10 g of n-propanol

Example 2

Production of an Aqueous Secondary Dispersion by Polymerization of N-vinylpyrrolidone with Stearyl Methacrylate in the Weight Ratio 7:3 in n-propanol The aqueous secondary dispersion was produced analogously to the procedure from example 1, differences to this being that feed 1 comprised 221 g of N-vinylpyrrolidone, 103 g of stearyl methacrylate and 240 g of n-propanol, and feed 3 had the following composition: 20 g of N-vinylpyrrolidone and 10 g of n-propanol. In this way, an aqueous secondary dispersion was obtained with a solids content of 16% by weight, which showed no signs of sedimentation or coagulation even after storage for four weeks at room temperature. The K value of the polymer (in accordance with Fikentscher see above, measured as 1% strength solution in ethanol at 25° C.) was 45.

Comparative Example 1

An aqueous secondary dispersion was produced analogously to the preparation procedure in example 1, differences to the procedure from example 1 being that no addition of feed 3 was undertaken and that feed 1 had the following composition: 241 g of N-vinylpyrrolidone, 103 g of stearyl methacrylate and 250 g of n-propanol. The secondary dispersion obtained displayed strong signs of sedimentation after four weeks at 25° C. The K value of the polymer was 45. The solids content of the dispersion was 15% by weight.

Comparative Example 2

The aqueous secondary dispersion was prepared analogously to the procedure from example 1, differences to this being that feed 3 comprised 46 g of polyvinylpyrrolidone with a K value of 12. The resulting aqueous secondary dispersion showed significant signs of sedimentation after four weeks. The K value of the polymer was 45. The solids content of the dispersion was 16% by weight.

Comparative Example 3

The aqueous secondary dispersion was prepared analogously to the procedure from example 1, differences to this being that feed 3 comprised 46 g of polyvinylpyrrolidone with a K value of 17. The resulting aqueous secondary dispersion showed clear signs of sedimentation after four weeks. The K value of the polymer was 44. The solids content of the dispersion was 16% by weight.

Comparative Examples 4 to 5

The aqueous secondary dispersion was prepared analogously to the procedure from example 2, with the following stipulations:

in comparative example 4, feed 3 comprised 20 g of polyvinylpyrrolidone with a K value of 12.

in comparative example 5, feed 3 comprised 20 g of polyvinylpyrrolidone with a K value of 17.

All of the resulting aqueous secondary dispersions showed clear signs of sedimentation after four weeks. The K value of the polymer was 45. The solids content of the dispersion was 16% by weight.

Example 3

Production of an Aqueous Secondary Dispersion by Polymerization of N-vinylpyrrolidone with Stearyl Methacrylate in the Weight Ratio 7:3 in n-propanol/water (8:2 v/v)

5 g of N-vinylpyrrolidone in a mixture of 70 g of n-propanol and 30 g of water were initially introduced into a polymerization vessel and heated to an internal temperature of 77° C. under a nitrogen atmosphere. Then, with stirring and while retaining the temperature, feed 1 was added over the course of 5.5 h and feed 2 was added over the course of 6.5 h. When feed 1 was complete, the addition of feed 3 was started over the course of 30 minutes. When feed 2 was complete, the temperature was maintained for a further 120 minutes. With the addition of water, a mixture of water and n-propanol was then started to be distilled off until the content of n-propanol in the distillation bottom had dropped to <1% by weight. In this way, an aqueous secondary dispersion with a solids content of 16% by weight was obtained, which showed no signs of sedimentation or coagulation even after storage for four weeks at room temperature. The K value of the polymer (in accordance with Fikentscher see above, measured as 1% strength solution in ethanol at 25° C.) was 44.

Feed 1: 229 g of vinylpyrrolidone, 120 g of stearyl methacrylate, 200 g of n-propanol, 42 g of water Feed 2:
2.85 g of tert-butyl peroxopivalate
46 g of n-propanol Feed 3:
46 g of N-vinylpyrrolidone
8 g of water

Example 4

The aqueous secondary dispersion was produced analogously to the procedure from example 3, differences to this being that feed 1 comprised 255 g of N-vinylpyrrolidone, 120 g of stearyl methacrylate, 200 g of n-propanol and 42 g of water, and feed 3 had the following composition: 20 g of N-vinylpyrrolidone and 8 g of water. In this way, an aqueous secondary dispersion with a solids content of 18% by weight was obtained, which showed no signs of sedimentation or coagulation even after storage for four weeks at room temperature.

Comparative Example 6

An aqueous secondary dispersion was produced analogously to the preparation procedure in example 3, differences to the procedure from example 3 being that no addition of a feed 3 was undertaken and feed 1 comprised 275 g of N-vinylpyrrolidone, 120 g of stearyl methacrylate, 200 g of n-propanol and 50 g of water. The resulting secondary dispersion showed strong signs of sedimentation after four weeks at 25° C. The K value of the polymer was 44. The solids content of the dispersion was 14% by weight.

Comparative Example 7

The aqueous secondary dispersion was produced analogously to the procedure from example 3, differences to this being that feed 3 comprised 46 g of polyvinylpyrrolidone with a k value of 12. The resulting aqueous secondary dispersion showed significant signs of sedimentation after four weeks. The K value of the polymer was 44. The solids content of the dispersion was 15% by weight.

Comparative Example 8

The aqueous secondary dispersion was produced analogously to the procedure from example 3, differences to this being that feed 3 comprised 46 g of polyvinylpyrrolidone with a K value of 17. The resulting aqueous secondary dispersion showed clear signs of sedimentation after four weeks. The K value of the polymer was 44. The solids content of the dispersion was 16% by weight.

Comparative Examples 9 to 10

The aqueous secondary dispersion was prepared analogously to the procedure from example 4, with the following stipulations:
  in comparative example 9, feed 3 comprised 20 g of polyvinylpyrrolidone with a K value of 12.
  in comparative example 10, feed 3 comprised 20 g of polyvinylpyrrolidone with a K value of 17.

All of the resulting aqueous secondary dispersions showed clear signs of sedimentation after four weeks. The K value of the polymer was 44. The solids content of the dispersion was 15% by weight.

Example 5

Production of an Aqueous Secondary Dispersion by Polymerization of N-vinylpyrrolidone with Stearyl Methacrylate in the Weight Ratio 7:3 in n-propanol/water (6:4 v/v)

The aqueous secondary dispersion was produced according to the procedure of example 3, the reaction medium being water/n-propanol in the weight ratio 4:6. The resulting secondary dispersion showed no signs of sedimentation or coagulation after storage for four weeks at room temperature. The K value of the polymer was 45. The solids content of the dispersion was 18% by weight.

Comparative Examples 11 and 12

The aqueous secondary dispersions were produced in accordance with the procedure of comparative examples 6 and 7, the reaction medium being water/n-propanol in the weight ratio 4:6. In all of the dispersions, severe coagulation was observed after four weeks at room temperature. The K value of the polymer was 45. The solids content of the dispersion was 16% by weight.

Example 6

Production of an Aqueous Secondary Dispersion by Polymerization of N-vinylpyrrolidone with Stearyl Methacrylate in the Weight Ratio 6:4 in n-propanol/water (8:2 v/v)

The aqueous secondary dispersion was prepared in accordance with the procedure of example 3, the weight ratio of N-vinylpyrrolidone to stearyl methacrylate being 6:4, based on the total amount of N-vinylpyrrolidone and stearyl methacrylate in the initial charge, feed 1 and feed 3. The resulting secondary dispersion showed no signs of sedimentation or coagulation after storage for four weeks at room temperature.

The K value of the polymer was 45. The solids content of the dispersion was 15% by weight.

Spray-Drying (General Procedure)

The aqueous dispersion was atomized via a single-material nozzle into the gas steam (cocurrent flow) of a spray-dryer. The gas inlet temperature was 180° C., the gas outlet temperature was 90-95° C. Using a second nozzle, pyrogenic silica (Aerosil 200, Degussa) was in an amount of 0.2-0.4% by weight, based on the polymer fraction of the dispersion.

In this way, in the case of the dispersion from example 1, a dry, flowable powder was obtained in a yield of >90%.

We claim:

1. A method of producing aqueous secondary dispersions of water-insoluble copolymers, comprising
    a) polymerization of ethylenically unsaturated monomers M by a free-radical solution polymerization in an organic, water-miscible solvent or in a mixture of water with an organic, water miscible solvent as polymerization medium, wherein the fraction of water in the mixture with the organic, water miscible solvent is not more than 30% by weight, where the monomers M comprise:
        i. 10 to 60% by weight, based on the total amount of monomers M, of at least one monoethylenically unsaturated monomer M1 with a solubility in water of not more than 10 g/l at 25° C. and 1 bar and
        ii. 40 to 90% by weight, based on the total amount of monomers M, of at least one hydrophilic, monoethylenically unsaturated, nonionic monomer M2 with a solubility in water of at least 80 g/l at 25° C. and 1 bar; and
    b) removing the organic solvent and adding water,
    wherein 1 to 20% by weight of the monomers M, based on the total amount of the monomers M, is a monomer composition M' comprising more than 90% by weight of the at least one hydrophilic, monoethylenically unsaturated, nonionic monomer M2 with a solubility in water of at least 80 g/l at 25° C. and 1 bar, and
    wherein the monomer composition M' is added to the polymerization medium after at least 80% of that fraction of monomers M which does not belong to the monomer composition M' has been added to the polymerization vessel under polymerization conditions.

2. The method according to claim 1, wherein the monomer composition M' provides 3 to 15% by weight of the total amount of the monomers M to be polymerized.

3. The method according to claim 1, wherein the polymerization of the monomers M takes place by a monomer feed method.

4. The method according to claim 1, wherein the hydrophilic, monoethylenically unsaturated, nonionic monomer M2 in the monomer composition M' is selected from N-vinyllactams having 5 to 8 ring atoms and N-vinylamides of aliphatic carboxylic acids having 1 to 6 carbon atoms and wherein the monomers M1 are selected from esters and amides of monoethylenically unsaturated carboxylic acids which have at least one hydrocarbon radical having 6 to 30 carbon atoms.

5. The method according to claim 4, wherein the monomer composition M' comprises more than 99% of N-vinylpyrrolidone.

6. The method according to claim 4, wherein the monomers M1 are selected from the group consisting of esters of acrylic acid with $C_8$-$C_{24}$-alkanols or $C_8$-$C_{24}$-cycloalkanols, esters of methacrylic acid with $C_8$-$C_{24}$-alkanols or $C_8$-$C_{24}$-cycloalkanols, the N—$C_8$-$C_{24}$-alkylamides and the N—$C_8$-$C_{24}$-cycloalkamides of acrylic acid and of methacrylic acid, and the N,N-bis($C_8$-$C_{24}$-alkyl)amides of acrylic acid and of methacrylic acid.

7. The method according to claim 1, wherein the polymerization is carried out in a $C_1$-$C_4$-alkanol or a mixture of a $C_1$-$C_4$-alkanol with water.

8. A method of producing aqueous secondary dispersions of water-insoluble copolymers, comprising
    a) polymerization of ethylenically unsaturated monomers M by a free-radical solution polymerization in an organic, water-miscible solvent or in a mixture of water with an organic, water miscible solvent as polymerization medium, wherein the fraction of water in the mixture with the organic, water miscible solvent is not more than 30% by weight, where the monomers M comprise:
        i. 15 to 50% by weight, based on the total amount of monomers M, of at least one monoethylenically unsaturated monomer M1 with a solubility in water of not more than 10 g/l at 25° C. and 1 bar and
        ii. 50 to 85% by weight, based on the total amount of monomers M, of at least one hydrophilic, monoethylenically unsaturated, nonionic monomer M2 with a solubility in water of at least 80 g/l at 25° C. and 1 bar; and
    b) removing the organic solvent and adding water,
    wherein 1 to 20% by weight of the monomers M, based on the total amount of the monomers M, is a monomer composition M' comprising more than 90% by weight of the at least one hydrophilic, monoethylenically unsaturated, nonionic monomer with a solubility in water of at least 80 g/l at 25° C. and 1 bar, and
    wherein the monomer composition M' is added to the polymerization medium after at least 80% of that fraction of monomers M which does not belong to the monomer composition M' has been added to the polymerization vessel under polymerization conditions.

9. The method according to claim 8, wherein the monomer composition M' provides 3 to 15% by weight of the total amount of the monomers M to be polymerized.

10. The method according to claim 8, wherein the polymerization of the monomers M takes place by a monomer feed method.

11. The method according to claim 8, wherein the addition of the monomer composition M' occurs after at least 90% by weight of the total monomers M have been added to the polymerization medium.

12. The method according to claim 8, wherein the hydrophilic, nonionic monomer in the monomer composition M' is selected from N-vinyllactams having 5 to 8 ring atoms and N-vinylamides of aliphatic carboxylic acids having 1 to 6 carbon atoms.

13. The method according to claim 12, wherein the monomer composition M' comprises more than 99% of N-vinylpyrrolidone.

14. The method according to claim 8, wherein the monomers M1 comprise at least 90% by weight of at least one monomer M1[a] with a solubility in water of not more than 1 g/l at 25° C. and 1 bar.

15. The method according to claim 8, wherein the monomers M1[a] are selected from esters and amides of monoethylenically unsaturated carboxylic acids which have at least one hydrocarbon radical having 6 to 30 carbon atoms.

16. The method according to claim 15, wherein the monomers M1[a] are selected from the group consisting of esters of acrylic acid with $C_8$-$C_{24}$-alkanols or $C_8$-$C_{24}$-cycloalkanols, esters of methacrylic acid with $C_8$-$C_{24}$-alkanols or $C_8$-$C_{24}$-cycloalkanols, the N—$C_8$-$C_{24}$-alkylamides and the N—$C_8$-$C_{24}$-cycloalkamides of acrylic acid and of methacrylic acid, and the N,N-bis($C_8$-$C_{24}$-alkyl)amides of acrylic acid and of methacrylic acid.

17. The method according to claim 8, wherein the monomers M, based on their total weight, comprise less than 0.1% by weight of monomers which have ionic or ionizable groups.

18. The method according to claim 8, wherein less than 0.5% by weight, based on the total weight of the monomers M added to the polymerization medium, are surfactants.

19. The method according to claim 8, wherein the polymerization is carried out in a $C_1$-$C_4$-alkanol or a mixture of a $C_1$-$C_4$-alkanol with water.

* * * * *